United States Patent [19]

Ewenson et al.

[11] Patent Number: 5,728,865
[45] Date of Patent: Mar. 17, 1998

[54] PROCESS FOR THE PREPARATION OF OCTYL P-METHOXY CINNAMATE

[75] Inventors: Ariel Ewenson, Omer; Bertha Croitoru; Asher Shushan, both of Beer-Sheva, all of Israel

[73] Assignee: Bromine Compounds Ltd., Beer-Sheva, Israel

[21] Appl. No.: 700,106

[22] Filed: Aug. 20, 1996

[30] Foreign Application Priority Data

Aug. 24, 1995 [IL] Israel ......................................... 115060
Jul. 8, 1996 [IL] Israel ......................................... 118817

[51] Int. Cl.$^6$ ......................................... C07C 69/76
[52] U.S. Cl. ......................................... 560/104; 560/105
[58] Field of Search ......................................... 560/104, 105

[56] References Cited

U.S. PATENT DOCUMENTS 5,187,303 2/1993 Eisenstadt et al. ......................................... 560/55

FOREIGN PATENT DOCUMENTS

WO 90/10617 9/1990 WIPO.
WO/94/05621 3/1994 WIPO.

OTHER PUBLICATIONS

Robert A. DeVries, Abel Mendoza, "Synthesis of High–Purity 0–and p–Vinyltoluenes by the Heck Palladium–Catalyzed Arylation Reaction", *Organometallics* 13, pp. 2405–2411 (1994).

N.A. Bumagin et al., "Palladium–catalyzed arylation of styrene and acrylic acid in water", *Journal of Organometallic Chemistry* 486, pp. 259–262 (1995).

Tuyet Jeffery, "Heck–type Reactions in Water", *Tetrahedron Letters*, vol. 35, No. 19, pp. 3051–3054 91994).

N.A. Bumagin et al., "Synthesis of substituted cinnamic acids and cinnamonitriles via palladium catalyzed coupling reactions of aryl halides with acrylic acid and acrylonitrile in aqueous media", *Journal of Organometallic Chemistry*, 371, pp. 397–401 (1989).

N.A. Bumagin et al., "Palladium–Catalyzed Arylation of Styrene in Water", *Doklady Akademii Nauk*, vol. 332, No. 4, pp. 454–456 (1993).

English version of N.A. Bumagin et al., "Palladium–Catalyzed Reactions of Acrylic Acid and Styrol with Aryl Halides in watr", *Zhurnal Organicheskoi Khimii*, 31, 4, pp. 481–487 (1995).

Harrison et al; Compendium of Organic Synthetic Methods, p. 273, 1971.

*Primary Examiner*—Gary Geist
*Assistant Examiner*—Sreeni Padmanabhan
*Attorney, Agent, or Firm*—Merchant, Gould, Smith, Edell, Welter, & Schmidt, P.A.

[57] ABSTRACT

A process for the preparation of octyl p-methoxy cinnamate is provided. The procedure generally concerns reacting p-bromo anisole with acrylic acid; and esterifying the resulting product with 2-ethyl hexanol. Preferred reactants and conditions are provided.

50 Claims, No Drawings

PROCESS FOR THE PREPARATION OF OCTYL P-METHOXY CINNAMATE

FIELD OF THE INVENTION

The present invention relates to a process for the preparation of a certain ester of substituted cinnamic acid, namely, octyl p-methoxy cinnamate, via the coupling of aryl halide to acrylic acid.

BACKGROUND OF THE INVENTION

Several methods are known in the art for the production of octyl p-methoxy cinnamate, a compound of great commercial importance. Octyl p-methoxy cinnamate, which is represented by formula I,

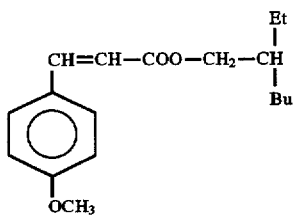

is used as a central ingredient in the industry of sunscreener products.

The key route in the synthesis of octyl p-methoxy cinnamate, according to some of the procedures taught by the art, involves a palladium catalyzed coupling reaction of aryl halide and an acrylic acid or ester thereof. The palladium plays an essential role in this kind of chemistry, because it is the arylpalladium complex, when formed, that reacts with the olefin (in the present discussion, the olefin is the acrylic acid). However, these procedures are all characterized by some typical drawbacks, which are mainly reflected in the solvents involved and amounts of catalysts or co-catalysts needed to accomplish the coupling reaction, as hereinafter described.

The reactions disclosed by the prior art are usually carried out in a variety of organic solvents, such as dimethylformamide, N,N-dimethylacetamide, dimethylsulfoxide and N-methylpyrrolidone, wherein anisole, substituted with halogen in a para orientation, is brought into contact with the acrylic acid or a derivative thereof, in the presence of a palladium catalyst such as Pd/C or $Pd(OAc)_2$. For example, WO 90/10617 describes the direct reaction of p-iodoanisole with several ester derivatives of an acrylic acid, with triethylamine and Pd/C. IL 97850 (corresponding to U.S. Pat. No. 5,187,303) more specifically discloses the direct reaction of bromo anisole with $CH_2=CH-COOCH_2-CHEtBu$, in an inert solvent, preferably an organic aprotic solvent (N-methylpyrrolidone). The palladium catalyst used was Pd/C or $Pd(OAc)_2$. The homogeneous catalysis was characterized by the presence of a co-catalyst (tri-phenyl phosphine). The molar ratio catalyst: co-catalyst: substrate was, according to IL 97850, approximately 2:1:500.

Therefore, the procedures according to the prior art, although part of them involve only one single step, namely, the vinylation reaction of the anisole derivative, require solvents which are expensive and often hazardous. The purity of the product, of course, is oftenly reduced due to the use of such solvents. The catalytic system described in the known procedures is based on relatively large amounts of catalysts and co-catalysts and comprise some other potentially problematic work-up stages: catalyst recovery might entail several not very straightforward washing sequences in this type of chemistry. All this indicates clearly that there is a need for a new, improved process for the preparation of octyl p-methoxy cinnamate.

It is therefore an object of the present invention to provide an ecologically clean and safe synthesis process for the preparation of octyl p-methoxy cinnamate, in good yields and with a very high degree of purity.

It is another object of the present invention to provide a process which is also economically advantageous and industrially convenient, characterized in that it requires only small amounts of catalysts and/or co-catalysts, and is completed in relatively short periods of time. The simple reaction of the catalytic system constitutes an important aspect of the present invention.

It is yet another object to provide a process which is applicable for an industrial scale, i.e., characterized by conditions that enable working in high concentrations of reactants.

It is another object of the present invention to provide an economically advantageous process, wherein the reaction can be effectively accomplished even in the presence of relatively low excesses of some of the reactants, the reaction further being characterized by a high volumetric yield and an improved energy consumption.

Other objects and advantages of the invention will become apparent as the description proceeds.

SUMMARY OF THE INVENTION

Surprisingly, it has now been found that it possible to prepare octyl p-methoxy cinnamate by following a two-step process, without the use of organic solvents. The first step involves reacting p-bromo anisole with acrylic acid in water, in the presence of a base, under certain condition of catalysis, temperature and pressure. The second step involves the preparation of octyl p-methoxy cinnamate, via an esterification of p-methoxy cinnamic acid obtained in the first stage, with 2-ethyl hexanol.

The process of the invention for the preparation of octyl p-methoxy cinnamate of formula I,

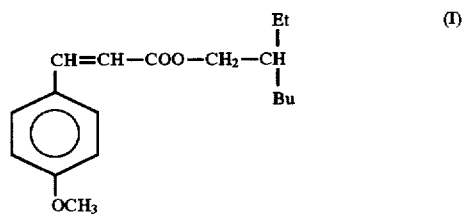

comprises the following steps:

a) reacting p-bromo anisole of formula II,

with acrylic acid or salts thereof in water as a solvent, the molar concentration of each of said reactants is higher than 0.1M, in the presence of a base and a palladium-based catalytic system, the molar ratio of the palladium catalyst of said catalytic system and of the para-bromo anisole being in the range of 1:200 to 1:90000, under elevated temperatures and autogenous pressure, to obtain p-methoxy cinnamic acid of formula III,

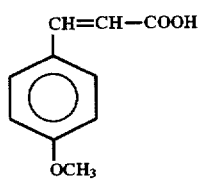

(III)

b) esterifying the p-methoxy cinnamic acid of formula III with a 2-ethyl hexanol of formula IV:

(IV)

Preferably, the p-methoxy cinnamic acid of formula (III), obtained in step a), is purified by washing with 2-ethylhexanol or by recrystallization therefrom, before the esterification stage is performed.

According to one embodiment of the invention, the base used in step a) is an inorganic base, preferably selected from among hydroxides, carbonates and phosphates. Most preferably $K_2CO_3$, alone or together with KOH, is used. Typically, 0.5 to 4 moles of inorganic base are used per mole of p-bromo anisole.

A preferred range of temperatures at which step a) is carried out in the presence of an inorganic base is 135° C.–190° C., more preferred is a range of 140° C.–160° C. Most preferably, the reaction is carried out at about 150° C.

In a preferred embodiment according to the present invention, the base applied in step a) is an organic base, preferably a tertiary amine, most preferably a trialkyl amine compound such as, for example, triethylamine.

Preferably, between about 2 to 4 moles of organic base are used per mole of p-bromoanisole, and most preferred is a ratio of 2.8:1.

Preferably, when the base applied in step a) is an organic base, the molar concentration of p-bromo anisole and acrylic acid is higher than 0.8M. Preferably, the molar ratio between the acrylic acid and p-bromo anisole is comprised between 1.5:1 and 1:1. Most preferred is a molar ratio of about 1.2:1.

Preferably, when the base applied in step a) is an organic base, the reaction of step a) is carried in the temperature range from 110° C.–150° C. A more preferred temperature range is from 120° C.–140° C., and most preferably the reaction is carried out at a temperature of about 125° C.–135° C.

The term "palladium-based catalytic system" is herein used to define a catalytic system which comprises a catalytically active palladium compound, and, optionally, a co-catalyst and/or phase transfer catalyst. A palladium compound may be, for example, a palladium salt or a supported palladium prepration. Typically, the molar ratio of the palladium catalyst to the p-bromo anisole is in the range of 1:200 to 1:40000.

According to one preferred embodiment of the invention, the palladium-based catalytic system involves palladium salts, such as $PdCl_2$ or $Pd(Ac)_2$. Preferably, the molar ratio of the palladium catalyst to p-bromo anisole is in the range of 1:10000 to 1:30000, most typically at about 1:22000, when said salts are used. Another useful palladium-based catalytic system, applicable for step a), comprises a palladium compound selected from among supported palladium preparations, such as, for example, a carbon supported palladium, herein defined as Pd/C, palladium on alumina, palladium on $BaSO_4$, or palladium on known polymeric supports, together with a co-catalyst. Without to be bound to any chemical theory, the typical co-catalyst is a palladium complexing agent. In another embodiment, a phase transfer catalyst is integrated to the above described catalytic system. The molar ratio of palladium supported preparation, such as Pd/C, to p-bromo anisole is, preferably, in the range of 1:1000 to 1:8000, most typically at about 1:3200.

Suitable temperatures for performing step b) are within the range of from approximately 110° C. to 170° C., especially a temperature of about 145° C. is preferred. In another embodiment, the esterification according to Step b) is carried out under reduced pressure in the range between 50 to 150 mbar, at a temperature range from approximately 90° C. to 130° C., most preferably at temperature of about 105° C. to 110° C. A strong acid is preferably used to catalyze the esterification according to both embodiments described above.

DETAILED DESCRIPTION OF THE INVENTION

The process for the preparation of octyl p-methoxy cinnamate according to the present invention is a two-step process. In the first step, reaction of p-bromo anisole with acrylic acid is carried out in water, the molar concentration of each of said reactants is higher than 0.1M, to obtain p-methoxy cinnamic acid in high purity, in the presence of a base and a palladium-based catalytic system, the molar ratio of the palladium catalyst of said catalytic system and of the para-bromo anisole being in the range of 1:200 to 1:90000, under elevated temperature and autogenous pressure. In the second step, p-methoxy cinnamic acid is esterified with 2-ethyl hexanol. The desired octyl p-methoxy cinnamate is finally obtained in an excellent yield and high purity.

According to one preferred embodiment of the invention, a very pure p-methoxy cinnamic acid is used in the esterification stage, which may be obtained by washing the product of the first step with 2-ethyl-hexanol or by recrystallization therefrom. The purified p-methoxy cinnamic acid, when esterified according to step b) with the same alcohol, gave the final product, octyl p-methoxy cinnamic acid, in a very high degree of purity. In this way, further steps of distillation which involve high temperatures and vacuum, and are usually required to comply with the chemical specifications of commercial octyl p-methoxy cinnamate, may be avoided.

According to one embodiment of the invention, the base which is present in the reaction mixture of step a) is an inorganic base, generally a hydroxide, a carbonate or a phosphate, such as KOH, NaOH, $K_2CO_3$, $Na_2CO_3$, $K_3PO_4$, $Na_3PO_4$. Combinations of said bases may be added to the solution. Preferably, $K_2CO_3$ is used, alone or together with potassium hydroxide. Typically, 0.5 to 4 moles of base are used per mole of p-bromo anisole.

The reaction of step a), when an inorganic base is present, is carried out under autogenous pressure and at any temperature in the range between 135° C.–190° C. Preferably, a temperature in the range of 140° C.–160° C. is employed, and the most preferred is 150° C. The mixture is stirred during the process, and usually a period of time of 1 to 7 hours is needed to accomplish the reaction.

In another preferred embodiment of the present invention, the base which is present in reaction mixture of step a) is an organic base, generally a tertiary amine, and most preferably a trialkyl amine such as, for example, triethylamine. If desired, operating with an organic base allows the reaction to proceed even at lower temperatures than these specified above, and, if desired, with higher concentrations of reactants, as will be hereinafter better explained. Tertiary amines, such as triethylamine are advantageous since they can form a binary mixture with the water, thereby providing an excellent medium for the isolation of the p-methoxy cinnamic acid in a very pure form. Preferably, between 2 and 4 moles of base are used per mole of p-bromo anisole, and most preferred is a molar ratio of about 2.8:1. The organic base may be successfully recovered by basic treatment of the acidified reaction mixture once the product is filtered off. The base can then be used in a subsequent reaction, without diminishing the reaction rate or product quality.

The reaction of step a), when an organic base is present, is preferably carried out at a temperature in the range from 110° C. to 150° C. Within this range, the preferred temperature range for carrying out the reaction is from 120° C. to 140° C., and particularly preferred is a temperature of about 125° C.–135° C. The mixture is stirred during said step, and usually a period of time of 1 to 4 hours is needed to accomplish the reaction.

The reaction of step a) may be accomplished in a wide range of concentrations of p-bromo anisole and of acrylic acid, the lower limit of said range for each of the said reactants is 0.1M. However, as taught by the examples and as would be recognized by one skilled in the art, the reaction rate decreases when said concentrations increase. When the base involved in the reaction mixture is an organic base, a higher volumetric yield can be obtained, as it has been found that relatively high concentrations can be used without impairing the kinetics. It is preferable to apply molar concentrations of p-bromo anisole and acrylic acid which are higher than 0.8M, when an organic base is used in step a). Preferably, the molar ratio between the acrylic acid and p-bromo anisole is comprised between 1.5:1 to 1:1. Most preferred is a molar ratio of about 1.2:1.

The reaction of step a) is efficiently catalyzed by a palladium-based catalytic system, as hereinabove defined. The components of the said catalytic system are determined by the type of palladium compound comprised in said catalytic system. Preferably, the molar ratio of the palladium catalyst to p-bromoanisole is in the range between 1:200 to 1:40000.

According to one most preferred embodiments, palladium salts such as PdCl$_2$, or Pd(Ac)$_2$ have been found to be extremely suitable as the palladium compound to be included in the catalytic system, because when palladium salts are used, no additional support in the form of co-catalysts or phase transfer catalysts is needed in the catalytic system. Typically, the molar ratio of the palladium catalyst to the p-bromanisole is in the range of 1:10000 to 1:80000, most preferred is a ratio of about 1:22000.

According to another embodiment of the invention, the palladium-based catalytic system may comprise other compounds of palladium, such as palladium supported preparations, together with co-catalysts. Typical examples for palladium supported preparations are Pd/C, palladium on alumnia, palladium on BaSO$_4$, or palladium on known polymeric supports. Most typically, Pd/C is used. An appropriate molar ratio between the palladuim catalyst and the p-bromo anisole in these cases is in the range of about 1:1000 to 1:8000. Suitable co-catalysts to be combined in the catalytic systems in these cases are palladium complexing agents, such as phosphines, ketones, nitriles and amides. Characteristic examples are compounds such as N-methyl pyrrolidone, tri-phenyl phosphine and 3-picoline. Typical molar ratio of the palladium catalyst: p-bromoanisole: co-catalyst is in the range of about 1:9.000:130 to 1:6000:300, most preferred is a ratio of about 1:32.00:160. It was surprisingly discovered, and this is another preferred embodiment of the invention, that when the catalytic system is based on said palladium supported preparations, a most efficient co-catalyst is N-methyl Pyrrolidone, where relatively small amounts of said co-catalyst are sufficient to accomplish the catalysis and to obtain excellent results, thus avoiding the use of toxic co-catalysts.

As mentioned, the catalytic systems described above can be further supported by phase transfer catalysts. Polyethylene glycol 600 is an excellent component for this purpose. Therefore, another preferred composition of the palladium-based catalytic system involves palladium supported preparation such as Pd/C as the palladium compound, N-methyl-pyrrolidone as a co-catalyst and Polyethylene glycol 600 as a phase transfer catalyst.

In order to isolate the product of step a), i.e., the p-methoxy cinnamic acid, the reaction mixture is cooled to about 50° to 90° C., filtered to remove the catalyst and the filtrate is acidified to pH of about 1 by means of concentrated acid, typically HCl or H$_2$SO$_4$. The precipitate which forms is collected. Usually, the purity of p-methoxy cinnamic acid obtained is higher than 97% (by HPLC), the yield is about 80–90%. Another advantage of the method according to the present invention is that the acrylic acid, although initially present in excess, poses no problem since it remains in the aqueous mother liquor. According to another preferred embodiment of the present invention, when step a) is carried out in the presence of a base which is an organic base, said excess may be reduced. As explained above, the product may now be purified by washing with 2-ethyl hexanol or by recrystallization therefrom, the alcohol to be used in the esterification stage. This purification, which is a further advantage of the present invention, leads to a very high degree of purity of the final, desired product, obtained through the second step. The degree of purity which characterizes the octyl p-methoxy cinnamate obtained is high enough to avoid the necessity for further distillation procedures.

The second step of the process involves an esterification of p-methoxy cinnamic acid, which is obtained from the first step with excellent purity ( due to the fact that its preparation is carried out in water and furthermore, due to the washing or recrystallization step which it is subjected to). The reaction of p-methoxy cinnamic acid with 2-ethyl hexanol can be carried out at temperatures between 110° C.–170° C., preferably at 145° C. Typically, an acid catalyst is present, such as sulfuric acid or sulfonic acids, for example. para-toluene sulphonic acid hydrate. A suitable range of molar ratio of p-methoxy cinnamic acid to 2-ethyl hexanol is 1:1 to 1:4. Preferably, a molar ratio of 1:2 is practiced. In order to facilitate the separation of phases in the azeotropic removal of water, a suitable water immiscible solvent having a boiling point between 90° C.–170° C., such as toluene or dibromomethane, may be added to the reaction mixture of step b), in order to limit the reaction temperature.

In another preferred embodiment, the reaction can be carried out under reduced pressure, in the range of about 50 to 150 mbar, at temperatures which are typically lower than specified above, in the presence of higher excess of 2-ethyl hexanol. These conditions allow the azeotropic removal of water obtained through the esterification even without adding a water immiscible solvent as described above. The molar ratio between p-methoxy cinnamic acid and 2-ethyl hexanol is between 1:4 to 1:7, preferably about 1:6, and the temperature employed is in the range between 90° C. to 130° C., preferably between 105° C. to 110° C. The esterification according to this embodiment is preferably catalyzed by a strong acid as described above and accomplished within 5 to 10 hours, providing a crude octyl p-methoxy cinnamate in an excellent purity and high stage yield.

As evidenced by Examples, when it is attempted to synthesize octyl p-methoxy cinnamate in water via direct coupling of p-bromo anisole and octyl acrylate, poor yield is obtained. Conducting the preparation of octyl p-methoxy cinnamate as a two-step process without using organic solvents, according to the present invention, combines several unexpected advantages. The use of water in step a), in a combination of certain conditions of temperature of pressure, besides being a clear and obvious advantage from the ecological and safety points of view, brings about a great improvement in the catalytic system, which is reflected in a significant reduction in the quantities of the palladium catalysts required, and, in some cases, in obviating the need for co-catalysts, and enables working in high concentrations of reactants. These improvements, as will be easily recognized by one skilled in the art, are of great industrial importance. Furthermore, the fact that no organic solvents are used ensures a better degree of purity of the products, and makes for a more economically advantageous process. According to the present invention, the purity of the final octyl p-methoxy cinnamate may be improved, because it was found out by the inventors that a simple purification procedure, when combined between the steps of the process, may bring a higher degree of purity to the final product.

All the above and other characteristics and advantages of the invention will be better understood through the following illustrative and non-limitative description of preferred embodiments thereof.

EXAMPLE 1

Preparation of octyl p-methoxy cinnamate

Step a):

Catalytic system: $PdCl_2$

Bases: $KOH+K_2CO_3$

Into a mechanically stirred, jacketed autoclave was fed a solution of Acrylic acid (73.6 gr., 1.02 mol) and KOH (85%, 63.2 gr, 0.98 mol) in water (600 mL.). $K_2CO_3$ (66.25 gr., 0.48 mole) was added followed by Palladium Chloride (5 mg) and 4-Bromo anisole (112 gr., 0.59 mol). The autoclave was sealed and heated to 150° C. (oil bath temperature) while stirring for five hours. At this point the heating was discontinued and the vessel was allowed to cool to 90° C. Upon opening, the catalyst was filtered off the mixture. An acidified aliquot of the filtrate was analyzed by qualitative HPLC showing a 90.2% conversion of 4-Bromo anisole to p-methoxy cinnamic acid. The filtrate is acidified to pH of about 1, by means of concentrated HCl. The precipitate which formed was collected.

Step b):

2.0 gr (12 mmol) of the crude p-Methoxy cinnamic acid, obtained in the previous stage with 98% purity was stirred with 2-Ethyl hexanol (3.1 gr, 24 mmol) in the presence of technical grade para Toluene sulfonic acid hydrate (115 mg, 0.6 mmol). The mixture was heated and stirred for one hour from 100° to 150° C. in a reaction vessel equipped with a condenser and a Dean-Stark apparatus.

The mixture was cooled to room temperature and an aliquot of the product was analyzed by qualitative HPLC, upon dilution with acetonitrile, showing:

| octyl p-methoxy cinnamate | 91.60% |
| p-methoxy cinnamic acid | 2% |
| Unknown impurities | 6.4% |

The crude product was dissolved with dichloroethane (10 mL) and twice washed with a 5% solution of $K_2CO_3$ in water (10 mL). The organic phase was twice washed with water (10 mL) and a sample thereof was analyzed by qualitative HPLC, showing:

| octyl p-methoxy cinnamate | 95% |
| p-methoxy cinnamic acid | 0.1% |
| Unknown impurities | 4.9% |

EXAMPLE 2

Preparation of octyl p-methoxy cinnamate

Step a):

Catalytic system: $PdCl_2$

Bases: $K_2CO_3$

Into a mechanically stirred, jacketed autoclave was fed a solution of Acrylic acid (73.6 gr., 1.02 mol) and $K_2CO_3$ (116 gr., 0.84 mole) in water (600 mL) followed by Palladium Chloride (5 mg) and 4-Bromo anisole (112 gr., 0.59 mol). The autoclave was sealed and heated to 150° C. (oil bath temperature) while stirring for 3.25 hours. The heating was discontinued and the vessel was allowed to cool to 90° C. Upon opening, the catalyst was filtered off the mixture. An acidified aliquot of the filtrate was analyzed by qualitative HPLC showing a 89.3% conversion of 4-Bromo anisole to p-methoxy cinnamic acid. The filtrate was acidified to a pH of about 1, by means of concentrated HCl. The precipitate which formed was collected.

Step b):

The esterification stage was carried out according to the description given in example 1, giving essentially identical results as those described therein.

EXAMPLE 3

Preparation of octyl p-methoxy cinnamate

Step a):

Catalytic system: $PdCl_2$

Bases: $KOH+K_3PO_4.H_2O$

The procedure described in example 1 was performed by using a mixture of bases consisting of $K_3PO_4.H_2O$ (96 gr, 0.41 mol) and KOH (63.2 gr, 0.98 mol, 85%). After 3 hours the conversion to p-methoxy cinnamic acid was 65.3%.

Step b):

The esterification stage was carried out according to the description given in example 1, giving essentially the same results as those described therein.

EXAMPLE 4 (comparative)

Preparation of octyl p-methoxy cinnamate

Catalytic system: none

Bases: $KOH+K_2CO_3$

The above procedure described in example 1 with KOH and $K_2CO_3$ was repeated in the absence of $PdCl_2$. After 4 hours the conversion to p-methoxy cinnamic acid was less than 2%.

EXAMPLE 5 (comparative)

Preparation of Octyl 4-methoxy cinnamate via direct reaction in water between Octyl acrylate and 4-Bromo anisole Into a magnetically stirred autoclave was fed a solution of $K_2CO_3$ (4.1 gr, 30 mmol) in water (10 mL), 5% Pd on carbon (70 mg) and Triphenylphosphine (17 mg, 0.06 mmol). Octyl acrylate (4.6 gr, 25 mmol) was added followed by Polyethylene glycol 600 (0.5 gr) and 4-Bromo anisole (2.8 gr, 15 mmol). The autoclave was sealed and heated to 150° C. (oil bath temperature) while stirring for four hours.

At this point the heating was discontinued and the vessel was allowed to cool to room temperature. The catalyst was filtered off and an aliquot of the organic layer was diluted in acetonitrile and analyzed by qualitative HPLC. The composition of the sample was:

| Octyl 4-methoxy cinnamate | 29% |
|---|---|
| 4-Bromo anisole | 61% |
| Unknown impurities | 10% |

EXAMPLE 6

Preparation of octyl p-methoxy cinnamate

Step a):

Catalytic system: Pd/C, N-methyl pyrrolidone, polyethylene glycol 600

Bases: $K_2CO_3$

Into a magnetically stirred autoclave was fed a solution of $K_2CO_3$ (166 gr., 1.2 mole) in water (600 mL), 5% Pd on carbon (400 mg) and N-methyl pyrrolidone (3.2 g, 0.03 mol). Acrylic acid (73.6 gr., 1.02 mol) was added and dissolved followed by Polyethylene glycol 600 (10 gr.) and 4-Bromo anisole (112 gr., 0.59 mol). The autoclave was sealed and heated to 150° C. (oil bath temperature) while stirring for four and a half hours.

At this point the heating was discontinued and the vessel was allowed to cool to 90° C. Upon opening, the catalyst was filtered off the mixture. An acidified aliquot of the filtrate was analyzed by qualitative HPLC showing the following composition:

| p-methoxy cinnamic acid | 92.3% |
|---|---|
| Acrylic acid | 2% |
| 4-Bromo anisole | 2% |
| Unidentified impurities | 3.7% |

Step b):

The esterification stage was carried out according to the description given in example 1, giving essentially the same results as those described therein.

EXAMPLE 7

Preparation of octyl p-methoxy cinnamate

Step a):

Catalytic system: Pd/C, triphenyl phosphine, polyethylene glycol 600

Bases: $K_2CO_3$

Into a magnetically stirred autoclave was fed a solution of $K_2CO_3$ (8.3 gr, 60 mmol) in water (30 mL), 5% Pd on carbon (40 mg) and Triphenyl phosphine (34 mg, 0.12 mmol). Acrylic acid (3.7gr, 50 mmol) was added and dissolved followed by Polyethylene glycol (PEG) 600 (1 gr) and 4-Bromo anisole (5.6 gr, 30 mmol). The autoclave was sealed and heated to 150° C. (oil bath temperature) while stirring for two hours.

At this point the heating was discontinued and the vessel was allowed to cool to room temperature. Upon opening, the resulting semi solid was dissolved by adding a solution of $K_2CO_3$ (2 gr) in water (100 mL). The mixture was heated and the catalyst was filtered off. An acidified aliquot of the filtrate was analyzed by qualitative HPLC showing the following composition:

| p-methoxy cinnamic acid | 90.4% |
|---|---|
| Acrylic acid | 1.4% |
| 4-Bromo anisole | 2.4% |
| Unidentified impurities | 5.8% |

The heated filtrate(90° C.) was acidified with concentrated HCl to a pH less than 1, and the ensuing precipitate was collected by filtration after cooling to room temperature. The collected solid was washed with water (to pH 4.0), dried under reduced pressure to constant weight. Qualitative HPLC of the dried product showed 97.7% p-methoxy cinnamic acid; the yield was 4.4 gr (82%).

Step b):

The esterification stage was carried out according to the description given in example 1, giving essentially the same results as those described therein.

EXAMPLE 8

Preparation of octyl p-methoxy cinnamate

Step a):

Catalytic system: $PdCl_2$

Bases: $KOH+K_2CO_3$

Into a mechanically stirred, jacketed autoclave was fed a solution of Acrylic acid (73.6 gr., 1.02 mol) and KOH (85%, 63.2 gr, 0.98 mol) in water (600 mL.). $K_2CO_3$ (66.25 gr., 0.48 mole) was added followed by Palladium Chloride (5 mg) and 4-Bromo anisole (112 gr., 0.59 mol). The autoclave was sealed and heated to 150° C. (oil bath temperature) while stirring for five hours. At this point the heating was discontinued and the vessel was allowed to cool to 90° C. Upon opening, the catalyst was filtered off the mixture. An acidified aliquot of the filtrate was analyzed by qualitative HPLC showing a 90.2% conversion of 4-Bromo anisole to p-methoxy cinnamic acid. The filtrate was acidified to a pH of about 1, by means of concentrated HCl. The precipitate which formed was collected.

Purification of crude p-methoxy cinnamic acid:

Dried p-methoxy cinnamic acid (77 g, 0.43 mole, 94% pure by HPLC) and 2-ethyl hexanol (150 gr, 1.15 moles) were warmed to 140° C. with dissolution of the acid. The solution was cooled spontaneously and at 100° C. the acid began to crystallize. The mixture was separated by filtration at 30° C. with #41 Whatman paper. The cake (76.5 gr) was washed twice with cold 2-ethyl hexanol (50 ml each wash, 10° C.) and it was dried by suction. HPLC analysis of the cake showed 98% p-methoxy cinnamic acid.

The cake was reslurried with 2-ethyl hexanol (70 ml) for 0.5 hours at room temperature, it was filtered and washed with 2-ethyl hexanol (10 ml). The white cake weighed 74.5 g and it consisted of >99% pure p-methoxy cinnamic acid.

Crude, wet p-methoxy cinnamic acid (~3–5% water content by K. Fischer analysis, ~90% by HPLC) was also purified by the same method, using the same proportion of 2-ethyl hexanol, giving the same result as above. Reslurry of crude p-methoxy cinnamic acid of similar quality in 2-ethyl hexanol gave ~98% pure p-methoxy cinnamic acid.

Step b):

Into a 250 ml flask, provided with a mechanical stirrer, a reflux condenser and a Dean-Stark azeotropic distillation apparatus were fed the purified p-methoxy cinnamic acid of the previous step (27 g, 0.15 mole), 2-ethyl hexanol (39 g, 0.3 mole), toluene (40 ml) and para-toluene sulfonic acid hydrate (0.7 g, 0.0036 mole).

The mixture was warmed up and at 110° C. all the solids dissolved. At 120° C. bottoms temperature; vapours temperature: 100° C.) the azeotropic removal of water commenced. The reaction was continued at 120° C.–125° C. for four hours, when a sample, analyzed by HPLC showed less than 0.7% of starting material present.

The mixture was cooled to room temperature and washed three times with water (50 ml, each, to separate the p-toluene sulfonic acid, the pH of the washes going from 1 to 4), once with 2% $Na_2CO_3$ (50 ml) and twice with water (50 ml, to eliminate the residual base). The solvent and the excess alcohol were separated by distillation, and the crude octyl p-methoxy cinnamate, analyzed by HPLC was >99% pure, with only one (heavier) impurity. Quantitive GC of the product gave 97.1%, containing besides the unknown impurity, ~2% of ethyl hexanol. The yield was 43 g (96% step yield).

EXAMPLE 9

Preparation of octyl p-methoxy cinnamate at various temperatures

The reaction of step a) was carried out at various temperatures. The other reaction parameters were as follows:

p- bromoanisole: 1 equivalent.; acrylic acid: 1.7 equivalents.; $K_2CO_3$: 1.4 equivalents.; water: 30 ml.; $PdCl_2$: 0.000056 equivalent.; time: 2 hours.

Table I summarizes the results:

TABLE I

| No. | T (°C.) | p-methoxy cinnamic acid (HPLC area %) | p-bromoanisole (HPLC area %) |
|---|---|---|---|
| 1 | 110 | 2.25 | 90 |
| 2 | 130 | 6.1 | 88 |
| 3 | 140 | 89 | 0.05 |
| 4 | 150 | 92.8 | 2.0 |
| 5 | 190 | 72 | 0.4 |

EXAMPLE 10

Preparation of octyl p-methoxy cinnamate in various ratios of p-bromo anisole:base The reaction of step a) was carried out in various ratios of p-bromo anisole:base, the base used was $K_2CO_3$.

The other reaction parameters were as follows:

p- bromo anisole- 30 mmole; acrylic acid- 45 mmole; water- 30 ml; $PdCl_2$:p-bromo anisole ratio- 1:21000; temperature- 150° C.; time- 2 hours.

Table II summarizes the results:

TABLE II

| No. | Base loading (mmole) | equivalent ratio to p-bromo anisole | conversion (HPLC area % of product, p-methoxy cinnamic acid) |
|---|---|---|---|
| 1 | 45 | 1.5 | 89.4 |
| 2 | 52.5 | 1.75 | 90.6 |
| 3 | 60 | 2.0 | 90.9 |

EXAMPLE 11

Preparation of octyl p-methoxy cinnamate in various concentrations of reactants The reaction of step a) was carried out in various concentrations of p-bromo anisole and acrylic acid.

The reaction parameters were as follows:

p- bromo anisolee- 0.6 mole; acrylic acid-1 mole; $PdCl_2$: p- bromo anisole ratio- 21000; temperature- 150° C.
Table III summarizes the results:

TABLE III

| No. | Water Volume (ml) | Time (hours) | conversion (HPLC area % of product, p-methoxy cinnamic acid) |
|---|---|---|---|
| 1 | 600 | 3.33 | 90.8 |
| 2 | 450 | 6.5 | 92.3 |

EXAMPLE 12

Preparation of p-octyl methoxy cinnamte in the presence of an organic base

Step a):

The following reagents: 12 g of water, 12.75 g of triethylamine (126 mmole), 8.4 g of p-bromo anisole (45 mmole), 3.9 g of acrylic acid (54 mmole) and 0.0003 g of palladium chloride were fed into a reaction autoclave and the vessel was sealed. The mixture was magnetically stirred and heated in an oil bath to 125°–130° C. for two hours.

The reaction vessel was cooled to about 50° C. and the catalyst was removed by filtration. The product, p-methoxy cinnamic acid, was isolated by precipitation from the clear reaction mixture with about 130 ml of $H_2SO_4$ (40%) and filtration.

The collected solid was washed with hot water, with 2-ethyl hexanol and dried. The yield was 6.7 g (83.8%) of 99% pure p-methoxy cinnamic acid. The purity of p-methoxy cinnamic acid was determined by qualitative HPLC.

Step b)

The following reagents were fed into a three necked reaction vessel, equipped with a mechanical stirrer, a distillation condenser, a receiving flask and a vacuum adapter: p-methoxy cinnamic acid (6.3 g, 35.5 mmole), 2-ethyl hexanol (24 g, 213 mmole) and para-toluene sulphonic acid (0.13 g).

The mixture was stirred and heated to 105° C. under 65 mbar vacuum for nine hours, while distilling off an azeotrope of 2-ethyl hexanol and water.

After cooling to room temperature, the crude product, as a 2-ethyl hexanol solution, weighted 29 g (33.2% p-octyl

13 methoxy cinnamate, assayed by quantitative GC, corresponding to 93.5% step yield). HPLC showed that the crude p-octyl methoxy cinnamate component was over 98% pure.

EXAMPLE 13

Preparation of p-methoxy cinnamic acid with a recycled organic base step a)

p-bromo anisole (8.4 g), acrylic acid (3.9 g), water (13.5 g), PdCl$_2$ (0.3 mg) and triethyamine (14.3 g, 89.3% pure by titration, the balance being water, recovered by phase separation from a previous run) were charged into an autoclave and heated for 2 hours at 130° C. The work up detailed in Example 1 gave 6.5 g (81%) of >98% pure p-methoxy cinnamic acid.

While embodiments of the invention have been described by way of illustration, it will be apparent that the invention can be carried out by persons skilled in the art with many modifications, variations and adaptations, without departing from its spirit or exceeding the scope of the claims. For example, various techniques may be employed during the esterification step in order to increase the quantity of ester formed.

We claim:

1. A process for the preparation of octyl p-methoxy cinnamate of formula I,

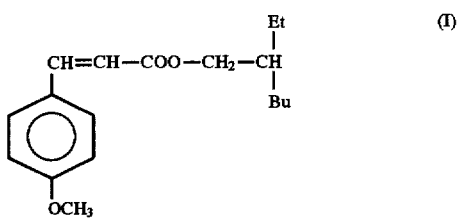

(I)

which comprises the following steps:

a) reacting p-bromo anisole of formula II,

(II)

with acrylic acid or salts thereof in water as a solvent, the molar concentration of each of said reactants is higher than 0.1M, in the presence of a base and a palladium-based catalytic system, the molar ratio of the palladium catalyst of said catalytic system and the p-bromo anisole being in the range of 1:200 to 1:90000, under elevated temperature and autogenous pressure, to obtain p-methoxy cinnamic acid of formula III,

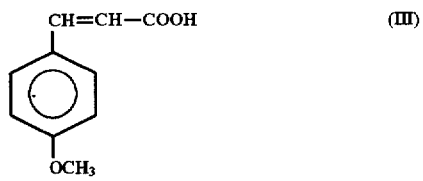

(III)

b) esterifying the p-methoxy cinnamic acid of formula III with a 2-ethyl hexanol of formula IV:

(IV)

2. A process according to claim 1, wherein the p-methoxy cinnamic acid obtained in step a) is purified through washing with 2-ethyl hexanol or recrystallization therefrom before the esterification stage.

3. A process according to claim 1, wherein the base is an inorganic base.

4. A process according to claim 3, wherein the base is of an hydroxide, a carbonate, a phosphate, or a combination of these bases.

5. A process according to claim 4, wherein the base is KOH, NaOH, K$_2$CO$_3$, Na$_2$CO$_3$, K$_3$PO$_4$, Na$_3$PO$_4$ or combinations thereof.

6. A process according to claim 5, wherein the base is K$_2$CO$_3$, alone or together with KOH.

7. A process according to claim 3, wherein step a) is carried out in a temperature of about 135° C.–190° C.

8. A process according to claim 7, wherein step a) is carried out in a temperature of about 140° C.–160° C.

9. A process according to claim 8, wherein step a) is carried out in a temperature of about 150° C.

10. A process according to claim 1, wherein the base is an organic base.

11. A process according to claim 10, wherein the organic base is a tertiary amine.

12. A process according to claim 11, wherein the tertiary amine is a trialkylamine.

13. A process according to claim 12, wherein the tertiary amine is triethylamine.

14. A process according to claim 10, wherein the reaction of step a) is carried out in the temperature range from 110° C. to 150° C.

15. A process according to claim 14, wherein the temperature is in the range from 120° C. to 140° C.

16. A process according to claim 15, wherein the temperature is in the range from 125° C. to 135° C.

17. A process according to claim 10, wherein the molar concentrations of p-bromo anisole and acrylic acid are higher than 0.8M.

18. A process according to claim 10, wherein the molar ratio between the acrylic acid and p-bromo anisole is comprised between 1.5:1 and 1:1.

19. A process according to claim 18, wherein the molar ratio between the acrylic acid and p-bromo anisole is about 1.2:1.

20. A process according to claim 1, wherein between 0.5 and 4 moles of base are used per mole of p-bromo anisole.

21. A process according to claim 1, wherein between 2 and 4 moles of base are used per mole of p-bromo anisole.

22. A process according to claim 21, wherein about 2.8 moles of base are used per mole of p-bromo anisole.

23. A process according to claim 1, wherein the molar ratio of the palladium catalyst included in the palladium-based catalytic system and the p-bromo anisole is in the range of 1:200 to 1:40000.

24. A process according to claim 1, wherein the palladium-based catalytic system comprises palladium salts selected from among PdCl$_2$ or Pd(OAc)$_2$.

25. A process according to claim 24, wherein the molar ratio of the palladium catalyst: p-bromo anisole is in the range of 1:10000 to 1:30000.

26. A process according to claim 25, wherein the molar ratio of the palladium catalyst: p-bromo anisole is about 1:22000.

27. A process according to claim 1, wherein the palladium-based catalytic system comprises palladium supported preparations as the palladium compound.

28. A process according to claim 27, wherein the molar ratio of the palladium catalyst: p-bromo anisole in the range of 1:1000 to 1:8000.

29. A process according to claim 28, wherein the molar ratio of the palladium catalyst: p-bromo anisole is about 1:3200.

30. A process according to claim 27, further comprising a co-catalyst in the palladium-based catalytic system.

31. A process according to claim 30, wherein the molar ratio palladium catalyst: p-bromo anisole: co-catalyst is in the range of 1:2000:130 to 1:6000:300.

32. A process according to claim 31, wherein the molar ratio palladium catalyst: p-bromo anisole:co-catalyst is about 1:3200:160.

33. A process according to claim 27, wherein the palladium supported preparation is selected from among Pd/C, palladium on alumina, palladium on $BaSO_4$, or Pd on polymeric supports.

34. A process according to claim 33, wherein the palladium supported preparation is Pd/C.

35. A process according to claim 30, wherein the co-catalyst is a palladium complexing agent.

36. A process according to claim 30, wherein the co-catalyst is ketone, phosphine, nitrile or amide.

37. A process according to claim 30, wherein the co-catalyst agent is selected from among tri-phenyl phosphine, n-methyl pyrrolidone or 3-picoline.

38. A process according to claim 37, wherein the co-catalyst is a n-methyl pyrrolidone.

39. A process according to claim 30, further comprises a phase transfer catalyst in the palladium-based catalytic system.

40. A process according to claim 39, wherein the phase transfer catalyst is poly ethylene glycol 600.

41. A process according to claim 40, wherein the palladium-based catalytic system comprises Pd/C, n-methyl pyrrolidone and polyethylene glycol 600.

42. A process according to claim 1, wherein step b) is carried out at a temperature range from 110° C.–170° C.

43. A process according to claim 42, wherein step b) is carried out at a temperature about 145° C.

44. A process according to claim 42, wherein the range of molar ratio of p-methoxy cinnamic acid to 2-ethyl hexanol is 1:1 to 1:4.

45. A process according to claim 44, wherein the range of molar ratio of p-methoxy cinnamic acid to 2-ethyl hexanol is about 1:2.

46. A process according to claim 1, wherein step b) is carried out under pressure in the range between 50 to 150 mbar and at a temperature in the range between 90° C. to 130° C., and the molar ratio between p-methoxy cinnamic acid and 2-ethyl hexanol used in step b) is comprised between 1:4 to 1:7.

47. A process according to claim 46, wherein the pressure is reduced to 65 mbar, temperature is about 105° C. and the molar ratio between p-methoxy cinnamic acid and 2-ethyl hexanol is about 1:6.

48. A process according to claim 1, wherein step b) is catalyzed by an acid.

49. A process according to claim 1, wherein water is removed azeotropically in step b).

50. Octyl p-methoxy cinnamate prepared according to the process of claim 1.

* * * * *

UNITED STATES PATENT AND TRADEMARK OFFICE
CERTIFICATE OF CORRECTION

PATENT NO. : 5,728,865

DATED : MARCH 17, 1998

INVENTOR(S) : EWENSON ET AL.

Page 1 of 2

It is certified that error appears in the above-identified patent and that said Letters Patent is hereby corrected as shown below:

Title page, [56] References Cited, Other Publications: "Tuyet Jeffery . . . 91994)." should read —Tuyet Jeffery . . . (1994).—

Title page, [56] References Cited, Other Publications: "English version . . . in watr" should read —English version . . . in water—

Col. 1, line 3: insert section —RELATED APPLICATIONS
A priority claim for the present application is made from Israel Application No. 115060, filed August 24, 1995; and Israel Application No. 118817, filed July 8, 1996. The complete disclosures of both are incorporated herein by reference.—

Col. 2, line 12: "simple reaction" should read —simplification—

Col. 5, line 51: "1:80000" should read —1:30000—

Col. 5, line 67: "1:9.000:130" should read —1:2000:130—

UNITED STATES PATENT AND TRADEMARK OFFICE
CERTIFICATE OF CORRECTION

PATENT NO. : 5,728,865
DATED : MARCH 17, 1998
INVENTOR(S) : EWENSON ET AL.

It is certified that error appears in the above-identified patent and that said Letters Patent is hereby corrected as shown below:

Col. 6, line 1: "1:32.00:160" should read --1:3200:160--

Col. 11, line 30: "ethyl hexanol" should read --2-ethyl hexanol--

Signed and Sealed this

Seventh Day of December, 1999

*Attest:*

Q. TODD DICKINSON

*Attesting Officer*     *Acting Commissioner of Patents and Trademarks*